(12) United States Patent
Moriya

(10) Patent No.: US 10,668,006 B2
(45) Date of Patent: Jun. 2, 2020

(54) COSMETIC AND METHOD FOR MANUFACTURING THE SAME

(71) Applicant: SHIN-ETSU CHEMICAL CO., LTD., Tokyo (JP)

(72) Inventor: Hiroyuki Moriya, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 20 days.

(21) Appl. No.: 15/676,040

(22) Filed: Aug. 14, 2017

(65) Prior Publication Data
US 2018/0071200 A1 Mar. 15, 2018

(30) Foreign Application Priority Data
Sep. 13, 2016 (JP) ................. 2016-178387

(51) Int. Cl.
| | | |
|---|---|---|
| A61K 8/895 | (2006.01) | |
| A61K 8/81 | (2006.01) | |
| A61K 8/894 | (2006.01) | |
| A61K 8/89 | (2006.01) | |
| A61K 8/87 | (2006.01) | |
| A61K 8/58 | (2006.01) | |
| A61K 8/91 | (2006.01) | |
| A61Q 1/06 | (2006.01) | |
| A61Q 1/02 | (2006.01) | |
| A61K 8/92 | (2006.01) | |

(52) U.S. Cl.
CPC ............ *A61K 8/895* (2013.01); *A61K 8/8152* (2013.01); *A61K 8/894* (2013.01); *A61K 8/91* (2013.01); *A61K 8/92* (2013.01); *A61Q 1/02* (2013.01); *A61Q 1/06* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 4,970,252 A | 11/1990 | Sakuta et al. | |
| 4,987,169 A | 1/1991 | Kuwata et al. | |
| 5,234,711 A * | 8/1993 | Kamen | A61K 8/11 106/31.65 |
| 5,236,986 A | 8/1993 | Sakuta | |
| 5,777,032 A * | 7/1998 | Yokoyama | C08J 7/12 525/123 |
| 2003/0199660 A1 | 10/2003 | Sakuta | |
| 2004/0234477 A1 | 11/2004 | Sakuta | |
| 2004/0253197 A1 | 12/2004 | Sakuta | |
| 2011/0171151 A1 | 7/2011 | Arnaud et al. | |
| 2013/0267478 A1 * | 10/2013 | Kamei | A61K 8/73 514/57 |

FOREIGN PATENT DOCUMENTS

| | | |
|---|---|---|
| EP | 0794440 A2 | 9/1997 |
| EP | 2647366 A2 | 10/2013 |
| JP | H02-43263 A | 2/1990 |
| JP | H02-214775 A | 8/1990 |
| JP | H06-116390 A | 4/1994 |
| JP | H09-136813 A | 5/1997 |
| JP | 2631772 B2 | 7/1997 |
| JP | H11-106310 A | 4/1999 |
| JP | 2000-063225 A | 2/2000 |
| JP | 2001-278732 A | 10/2001 |
| JP | 2001-342255 A | 12/2001 |
| JP | 2006-282585 A | 10/2006 |
| JP | 2009-185296 A | 8/2009 |
| JP | 2012-502018 A | 1/2012 |
| JP | 2012-072081 A | 4/2012 |
| WO | 98/05269 A1 | 2/1998 |
| WO | 03/024416 A1 | 3/2003 |
| WO | 2003/020828 A1 | 3/2003 |
| WO | 2014/093772 A1 | 6/2014 |

OTHER PUBLICATIONS

Stone—RadTech e5 2004 Technical Proceedings (Year: 2004).*
JP H06 116 390 (A) in machine translation (Year: 1994).*
Oct. 20, 2017 Search Report issued in European Patent Application No. 17001414.6.
Jun. 18, 2019 Office Action issued in Japanese Application No. 2016-178387.

* cited by examiner

*Primary Examiner* — Monica A Shin
(74) *Attorney, Agent, or Firm* — Oliff PLC

(57) ABSTRACT

Disclosed is a cosmetic that provides smooth spreadability, non-stickiness upon application, suppressed color transfer as a make-up cosmetic, and easy removability by cleansing. The cosmetic of the invention includes a urethane group-containing silicone vinyl polymer that is a urethanization reaction product of a (a) radical polymer derived from a radical reactive vinyl monomer and having a hydroxyl group and an (b) isocyanate silicone represented by the following general formula (1),

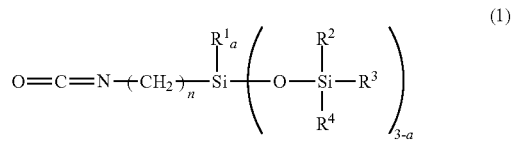

wherein, each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3.

12 Claims, No Drawings

COSMETIC AND METHOD FOR MANUFACTURING THE SAME

TECHNICAL FIELD

The present invention relates to a cosmetic and a method for manufacturing a cosmetic.

BACKGROUND ART

Conventionally there have been various known silicone-containing film formers. Particularly, various silicone-containing acryl polymers are obtained by copolymerization of a silicone-containing macromonomer and a radical reactive monomer. The resulting silicone-containing acrylic polymer is added to cosmetics for product improvement (Patent Literatures 1 to 5). The added silicone component can improve the flexibility of the resulting film and the solubility into an oil agent.

However, cosmetics including these silicone-containing acrylic copolymers, unfortunately, fail to provide satisfactory feeling on use such as smooth spreadability and non-stickiness, and to control color transfer (or secondary adhesiveness). One additional drawback is that make-up cosmetics such as powder/liquid foundations, using a silicone-containing acrylic copolymer, are difficult to remove. There has been a growing demand for the solution of these problems.

CITATION LIST

Patent Literature

PATENT LITERATURE 1: Japanese Patent Laid-Open Publication (Kokai) No. 2000-063225
PATENT LITERATURE 2: Japanese Patent Laid-Open Publication (Kokai) No. 2001-278732
PATENT LITERATURE 3: Japanese Patent Laid-Open Publication (Kokai) No. 2006-282585
PATENT LITERATURE 4: Japanese Translation of PCT International Application No. 2012-502018
PATENT LITERATURE 5: Japanese Patent Laid-Open Publication (Kokai) No. 2012-072081

SUMMARY OF INVENTION

Technical Problem

The present invention was made in view of the above situation to solve the problems with conventional silicone-containing acrylic film formers, and has an object to provide a cosmetic that provides smooth spreadability, non-stickiness upon application, suppressed color transfer as a make-up cosmetic, and easy cleansing removal, and a method for manufacturing the cosmetic.

Solution to Problem

To solve the problems mentioned above, the present invention provides a cosmetic including a urethane group-containing silicone vinyl polymer that is a urethanization reaction product of a (a) radical polymer derived from a radical reactive vinyl monomer and having a hydroxyl group and an (b) isocyanate silicone represented by the following general formula (1), $$O=C=N-(CH_2)_n-\underset{\underset{R^1}{|}}{Si}\left(-O-\underset{\underset{R^4}{|}}{\overset{\overset{R^2}{|}}{Si}}-R^3\right)_{3-a} \quad (1)$$

wherein, each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3.

The cosmetic provides smooth spreadability, non-stickiness upon application, suppressed color transfer as a make-up cosmetic, and easy removability by cleansing.

In this case, the (a) radical polymer preferably, as the radical reactive vinyl monomer, includes at least one radical reactive vinyl monomer having a hydroxyl group selected from any of hydroxyethyl (meth)acrylate, hydroxypropyl (meth)acrylate, glyceryl (meth)acrylate, and hydroxyethyl acrylamide.

Such a radical polymer including a radical reactive vinyl monomer having a hydroxyl group can readily be synthesized, and therefore be preferable.

In this case, the content of the unit derived from the isocyanate silicone represented by the general formula (1) in the urethane group-containing silicone vinyl polymer is preferably 40 wt % or more.

Such a urethane group-containing silicone vinyl polymer may assuredly be dissolved in an organic oil agent used in a cosmetic such as a silicone oil, and sufficiently be useful. Accordingly, the urethane group-containing silicone vinyl polymer can provide a flexible film and a cosmetic having more excellent cosmetic durability.

In this case, the urethane group-containing silicone vinyl polymer preferably includes at least one hydroxyl group.

The urethane group-containing silicone vinyl polymer can further improve the feeling of cosmetic quality, cosmetic durability, and emulsion stability.

In this case, the content of the urethane group-containing silicone vinyl polymer is preferably 0.05 to 40 wt %, relative to the total amount of the cosmetic.

Such a cosmetic provides further smooth spreadability, non-stickiness upon application, suppressed color transfer as a make-up cosmetic, and easy removability by cleansing, and therefore be preferable.

Preferably, the cosmetic of the present invention further includes a silicone oil.

The urethane group-containing silicone vinyl polymer of the present invention is a hard substance that can be dissolved into a silicone oil. Therefore, the urethane group-containing silicone vinyl polymer can be advantageously blended in a cosmetic as a film former.

Preferably, the cosmetic further includes water, and is in the form of an emulsion.

This type of cosmetic may preferably be e.g., a make-up base, a liquid foundation, a sunscreen emulsion, and a sunscreen cream.

Preferably, the cosmetic further includes a powder, and is in the form of a liquid, a paste or a solid, with the powder dispersed therein.

This addition of a powder makes a cosmetic application more suitable.

Also, the present invention provides a method for manufacturing a cosmetic including, in the order mentioned, the steps of:
(A) obtaining a radical polymer having a hydroxyl group by radical polymerization of a radical reactive vinyl monomer,
(B) obtaining a urethane group-containing silicone vinyl polymer by urethanization reaction of the radical polymer having a hydroxyl group and an isocyanate silicone represented by the following general formula (1) in the presence of a urethanization catalyst,

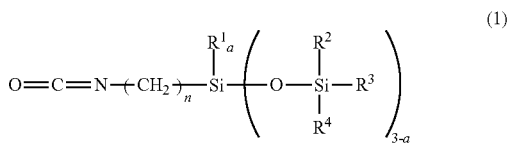

(1)

wherein, each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3; and
(C) obtaining a cosmetic by using the urethane group-containing silicone vinyl polymer.

The method for manufacturing a cosmetic can provide a cosmetic having smooth spreadability, non-stickiness upon application, suppressed color transfer as a make-up cosmetic, and easy removability by cleansing.

In this case, in the step (A), at least one monomer selected from any of hydroxyethyl (meth)acrylate, hydroxypropyl (meth)acrylate, glyceryl (meth)acrylate, and hydroxyethyl acrylamide is preferably used as the radical reactive vinyl monomer.

The radical polymer having a hydroxyl group can be obtained more easily by using such a radical reactive vinyl monomer, and hence these monomers are preferable.

In this case, the urethanization catalyst may preferably be a tertiary amine.

In cases where a catalyst is not added during urethanization reaction, the reaction rate decreases and the yield is reduced. In view of easy removability by cleansing, the urethanization catalyst may preferably be a tertiary amine.

Advantageous Effects of Invention

The urethane group-containing silicone vinyl polymer as part of the cosmetic of the present invention and the urethane group-containing silicone vinyl polymer obtained in the method for manufacturing the cosmetic of the present invention are hard substances that are dissolved into an oil agent such as a silicone oil. Therefore, the urethane group-containing silicone vinyl polymer can be blended in a cosmetic as a film former. The resulting cosmetic provides smooth spreadability and excellent feeling on use as refreshing feeling, sufficiently suppressed color transfer as a make-up cosmetic, and easy removability by cleansing. In addition, a urethane group-containing silicone vinyl polymer which includes not only a urethane group but also a hydroxyl group in a molecule may act as an emulsion stabilizer to enhance emulsion stability, improve the affinity with a powder, and provide more excellent feeling on use.

DESCRIPTION OF EMBODIMENTS

The present inventors have earnestly carried out investigations to accomplish the above-mentioned object, and as a result, they have found that a cosmetic including a certain urethane group-containing silicone vinyl polymer provides smooth spreadability, refresh and excellent feeling, suppressed color transfer as a make-up cosmetic, and easy cleansing removal. Based on that information, the present invention was accomplished. The cosmetic of the present invention and the method for manufacturing the cosmetic of the present invention will be described in detail.

The cosmetic of the present invention includes a urethane group-containing silicone vinyl polymer that is a urethanization reaction product of a (a) radical polymer derived from a radical reactive vinyl monomer and having a hydroxyl group and an (b) isocyanate silicone represented by the following general formula (1),

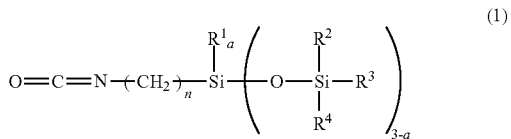

(1)

wherein, each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3.

(a) Radical Polymer

The (a) radical polymer constituting the urethane group-containing silicone vinyl polymer included in the cosmetic of the present invention is a radical polymer derived from at least one radical reactive vinyl monomer and having a hydroxyl group.

The radical reactive vinyl monomer is a vinyl monomer having a radical polymerizable carbon-carbon double bond. Illustrative example of the radical reactive vinyl monomer includes a lower alkyl (meth)acrylate such as methyl (meth)acrylate, ethyl (meth) acrylate, n-propyl (meth)acrylate, isopropyl (meth)acrylate, n-butyl (meth) acrylate, isobutyl (meth) acrylate, tert-butyl (meth)acrylate, n-hexyl (meth) acrylate, and cyclohexyl (meth)acrylate; a higher alkyl (meth)acrylate such as 2-ethylhexyl (meth) acrylate, octyl (meth) acrylate, lauryl (meth)acrylate, and stearyl (meth) acrylate; fatty acid vinyl ester such as vinyl acetate, vinyl propionate, vinyl butyrate, vinyl caproate, vinyl 2-ethylhexanoate, vinyl laurate, and vinyl stearate; an aromatic containing monomer such as styrene, vinyl toluene, benzyl (meth)acrylate, and phenoxyethyl (meth)acrylate; an amide group-containing monomer such as (meth)acrylamide, N-methylol (meth)acrylamide, N-methoxy methyl (meth) acrylamide, isobuthoxy methoxy (meth)acrylamide, N,N-dimethyl (meth)acrylamide, vinyl pyrrolidone, and N-vinyl acetamide; a hydroxyl group-containing monomer such as hydroxyethyl (meth)acrylate, hydroxypropyl (meth)acrylate, glyceryl (meth)acrylate, and hydroxyethyl acrylamide; an ether bond-containing monomer such as tetrahydrofurfuryl (meth) acrylate, buthoxyethyl (meth)acrylate, ethoxy diethylene glycol (meth)acrylate, polyethylene glycol (meth)acrylate, polypropylene glycol mono (meth)acrylate, hydroxybutyl vinyl ether, cetyl vinyl ether, and 2-ethylhexyl vinyl ether; a carboxylic acid-containing monomer such as (meth)acrylic acid, itaconic acid, crotonic acid, fumaric acid, and maleic acid; glycidyl (meth)acrylate, glycidyl ether (meth)allyl, and methacryloyloxyethyl isocyanate.

The (a) radical polymer in the present invention, having a hydroxyl group, essentially includes, as a monomer unit, a radical reactive vinyl monomer having a hydroxyl group. As the radical reactive vinyl monomer having a hydroxyl group, the above described radical reactive vinyl monomer can be used so long as the radical reactive vinyl monomer has a hydroxyl group, but preferably a hydroxyl group-containing monomer such as hydroxyethyl (meth) acrylate, hydroxypropyl (meth) acrylate, glyceryl (meth)acrylate, and hydroxyethyl acrylamide.

(b) Isocyanate Silicone Represented by General Formula (1)

The (b) isocyanate silicone represented by the following general formula (1) in the present invention is a component constituting the urethane group-containing silicone vinyl polymer by urethanization reaction with the (a) radical polymer,

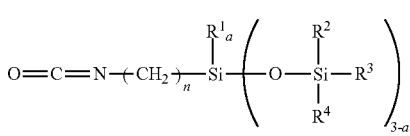

wherein, each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3.

In the general formula (1), "n" represents a number of 1 to 10, preferably 3. Each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms. Illustrative example of the alkyl group includes a methyl group, an ethyl group, a propyl group, a butyl group, a pentyl group, a hexyl group, a heptyl group, an octyl group, a cyclopentyl group, and a cyclohexyl group. Illustrative example of the aryl group includes a phenyl group and a tolyl group. Illustrative example of the fluorine-substituted alkyl group includes a trifluoropropyl group and a heptadeca fluorodecyl group. Preferably, $R^1$, $R^2$, $R^3$, and $R^4$ are a methyl group, an ethyl group, or a propyl group, particularly a methyl group. "a" represents a number of 0 to 3, preferably 0 or 1.

The cosmetic including the urethane group-containing silicone vinyl polymer that is a urethanization reaction product of the (a) radical polymer derived from a radical reactive vinyl monomer and having a hydroxyl group, and the (b) isocyanate silicone represented by the general formula (1) provides smooth spreadability, non-stickiness upon application, suppressed color transfer as a make-up cosmetic, and easy removability by cleansing.

Method for Manufacturing Cosmetic

The present invention provides a method for manufacturing a cosmetic including the steps of:

(A) obtaining a radical polymer having a hydroxyl group by radical polymerization of a radical reactive vinyl monomer, (B) obtaining a urethane group-containing silicone vinyl polymer by urethanization reaction of the radical polymer having a hydroxyl group and an isocyanate silicone represented by the following general formula (1) in the presence of a urethanization catalyst,

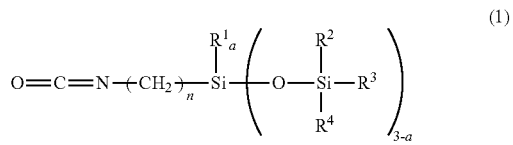

wherein, each of $R^2$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3; and (C) obtaining a cosmetic by using the urethane group-containing silicone vinyl polymer.

The radical reactive vinyl monomer used in the step (A) and the isocyanate silicone represented by the general formula (1) used in the step (B) may be the same as before.

The step (A) obtains a radical polymer having a hydroxyl group by radical polymerization of the radical reactive vinyl monomer. The radical polymerization preferably involves solution polymerization process. In this process the radical reactive vinyl monomer is reacted in a solvent in the presence of a radical initiator at 30 to 150° C., preferably at 50 to 120° C. for 1 to 20 hours, preferably 2 to 10 hours. Illustrative of the solvent includes an aliphatic hydrocarbon solvent such as hexane, octane, decane, dodecane, and cyclohexane; an aromatic hydrocarbon solvent such as benzene, toluene, and xylene; ethers such as diethyl ether, dibutyl ether, tetrahydrofuran, and dioxane; a ketones such as acetone, methyl ethyl ketone, methyl isobutyl ketone, and diisobutyl ketone; esters such as methyl acetate, ethyl acetate, butyl acetate, and isobutyl acetate; amides such as dimethylformamide, diethylformamide, dimethylacetamide, N methyl pyrrolidone, tetramethyl urea, and hexamethylphosphoric amide; alcohols such as methanol, ethanol, isopropyl alcohol, and butanol; and organosiloxane oligomer such as octamethylcyclotetrasiloxane, decamethylcyclopentasiloxane, hexamethyldisiloxane, and octamethyltrisiloxane. Particularly preferable are toluene, tetrahydrofuran, dioxane, methyl ethyl ketone, methyl isobutyl ketone, diisobutyl ketone, butyl acetate, isobutyl acetate, dimethylformamide, diethylformamide, dimethylacetamide, and N methylpyrrolidone.

The radical initiator is a known compound generally used in radical polymerization method. Illustrative example of the radical initiator includes an azobis-based compound such as 2,2'-azobis (isobutyronitrile), 2,2'-azobis(2-methylbutyronitrile), and 2,2'-azobis(2,4-dimethyl)valeronitrile; an organic peroxides such as benzoyl peroxide, lauroyl peroxide, tert-butyl peroxybenzoate, and tert-butylperoxy-2-ethylhexanoate though it is not restricted to these substances. What is preferable is 2,2'-azobis (isobutyronitrile), 2,2'-azobis(2-methylbutyronitrile), 2,2'-azobis(2,4-dimethyl)valeronitrile, and tert-butylperoxy-2-ethylhexanoate. These radical initiators may be used alone or in combination with 2 or more other ones.

The radical initiator is preferably used in an amount ranging from 0.1 to 10 parts by weight, relative to 100 parts by weight of a radical reactive vinyl monomer. In polymerization, a chain transfer agent can be added. Illustrative example of the chain transfer agent includes a mercapto compound such as 2-mercaptoethanol, butyl mercaptan, N-dodecyl mercaptan, 3-mercaptopropyltrimethoxysilane, and polydimethylsiloxane having a mercaptopropyl group;

and a halide such as methylene chloride, chloroform, carbon tetrachloride, butyl bromide, and 3-chloropropyltrimethoxysilane.

The radical polymer obtained in the step (A) includes a hydroxyl group, and the radical polymer preferably include, as the radical reactive monomer having a hydroxyl group, one or more kinds of hydroxyethyl (meth)acrylate, hydroxypropyl (meth)acrylate, glyceryl (meth)acrylate, or hydroxyethyl acrylamide. The radical reactive monomer having a hydroxyl group is a component required as a reaction site with an isocyanate in the following step (B). There is a method where radical polymerization process is followed by the reaction of the radical reactive monomer having a hydroxyl group and the isocyanate silicone represented by the general formula (1). This process, unfortunately, fails to remove the unreacted isocyanate silicone to cause polymer crosslinking during polymerization.

The radical polymer obtained in the step (A) may be subjected to refinement under reduced pressure, or refinement by reprecipitation, but preferably a reaction solution is subsequently used in the next step.

The step (B) obtains a urethane group-containing silicone vinyl polymer by urethanization reaction of the radical polymer having a hydroxyl group obtained in the step (A) and the isocyanate silicone represented by the general formula (1) in the presence of a urethanization catalyst.

In cases where a catalyst is not added in urethanization reaction, the reaction rate declines and the yield is reduced. Illustrative example of the catalyst includes an amines such as triethylamine, triethylenediamine, and N methylmorpholine; and an organic metal compound such as di-n-butyltin dilaurate, stannous oleate, and iron acetylacetonate complex. In view of easy cleansing removal, a tertiary amine is preferably used, particularly triethylamine. The reaction is achieved normally at 50 to 150° C., preferably 70 to 130° C. The reaction solvent is a solvent for the radical polymer obtained in the step (A) to dissolve, preferably an aprotic solvent, particularly preferably toluene, tetrahydrofuran, dioxane, methyl ethyl ketone, methyl isobutyl ketone, diisobutyl ketone, butyl acetate, isobutyl acetate, dimethylformamide, diethylformamide, dimethylacetamide, and N methylpyrrolidone.

Preferably, when the isocyanate silicone represented by the general formula (1) is reacted with the radical polymer having a hydroxyl group obtained by the step (A), the hydroxyl group is not entirely, but partially reacted. At least one residue hydroxyl group is included in the urethane group-containing silicone vinyl polymer obtained by the step (B) to help a hydrophilic site improve the affinity with a powder and further improve the feeling of cosmetic quality, cosmetic durability, and emulsion stability.

The urethane group-containing silicone vinyl polymer reaction solution obtained may be added to a poor solvent to be refined by reprecipitation.

In the step (C), the urethane group-containing silicone vinyl polymer is used to obtain a cosmetic. The resulting cosmetic provides smooth spreadability, non-stickiness upon application, suppressed color transfer as a make-up cosmetic, and easy removability by cleansing.

In the cosmetic of the present invention and the method for manufacturing the cosmetic of the present invention, the weight average molecular weight of the urethane group-containing silicone vinyl polymer in GPC in terms of polystyrene is preferably 700 to 300,000, more preferably 5000 to 200,000, and much more preferably 8000 to 100,000.

Preferably, the content of the unit derived from the isocyanate silicone represented by the general formula (1) in the urethane group-containing silicone vinyl polymer is 40 wt % or more, particularly 50 wt % or more. With a content of the unit derived from the isocyanate silicone of 40 wt % or more, solubility into an organic oil agent used in a cosmetic such as a silicone oil is preferably ensured and can sufficiently be useful. A film having sufficiently flexibility can be obtained and the resulting cosmetic has further improved cosmetic durability.

At least one hydroxyl group is preferably included in the urethane group-containing silicone vinyl polymer. The inclusion of at least one hydroxyl group can help a hydrophilic site improve the affinity with a powder and further improve the feeling of quality of cosmetic, cosmetic durability, and emulsion stability.

The content of the urethane group-containing silicone vinyl polymer is preferably 0.05 to 40 wt %, relative to the total amount of the cosmetic, more preferably 2 to 25 wt %. Accordingly, the cosmetic ensurely provides smooth spreadability, non-stickiness upon application, suppressed color transfer as a make-up cosmetic, and easy cleansing removal.

The cosmetic of the present invention, and the cosmetic obtained by the method for manufacturing the cosmetic of the present invention, other than a urethane group-containing silicone vinyl polymer, can include the following other components.

Preferably, the cosmetic of the present invention further includes a silicone oil. Illustrative example of the silicone oil includes low viscous to high viscous linear or branched organopolysiloxanes such as dimethyl polysiloxane, tristrimethyl cyloxymethylsilane, caprylyl methicone, phenyl trimethicone, tetrakis trimethylsiloxysilane, methyl phenyl polysiloxane, methylhexyl polysiloxane, methyl hydrogen polysiloxane, and dimethylsiloxane/methylphenylsiloxane copolymer; a cyclic organopolysiloxane such as octamethyl cyclotetrasiloxane, decamethyl cyclopentasiloxane, dodecamethyl cyclohexasiloxane, tetramethyl tetrahydrogen cyclotetrasiloxane, and tetramethyltetraphenyl cyclotetra siloxane; a silicone rubber such as an amino-modified organopolysiloxane, a pyrrolidone-modified organopolysiloxane, a pyrrolidone carboxylate-modified organopolysiloxane, a gum dimethyl polysiloxane with a high degree of polymerization, gum amino-modified organopolysiloxane, and gum dimethylsiloxane/methylphenylsiloxane copolymer; a silicone gum and rubber cyclic organopolysiloxane solution, a trimethylsiloxysilicate, a trimethylsiloxysilicate cyclic siloxane solution, and a higher alkoxy-modified silicone such as stearoxysilicone; a higher fatty acid-modified silicone, an alkyl-modified silicone, a long chain alkyl-modified silicone, an amino acid-modified silicone, a fluorine-modified silicone, a silicone resin and a melt of a silicone resin. Illustrative example of the fluorinated oil agent includes perfluoro polyether, perfluoro decalin, and perflouro octane.

Furthermore, the cosmetic of the present invention may include at least one oil agent according to the purpose thereof. Any oil agent may be used in the form of a solid, a semi-solid, or a liquid so long as it is used in a usual cosmetic. Illustrative example of the natural vegetable and animal fatty oil and the semi-synthetic oil includes an avocado oil, a linseed oil, an almond oil, an insects wax, a perilla oil, an olive oil, a cacao butter, a kapok wax, a kaya oil, a carnauba wax, a lever oil, a candelilla wax, a purified candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a Shea butter, a Chinese tung oil, a cinnamon oil, a jojoba wax, a squalane oil, a squalene oil, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse wax, a Persic oil, a palm oil, a palm kernel oil, a castor oil, a cured castor oil, a methyl ester of cured castor oil fatty acid, a sunflower oil, a grape seed oil, a bayberry wax, a jojoba oil, a macadamia nut oil, a bees wax, a mink oil, a meadow foam oil, a cotton seed oil, a cotton wax, a Japan wax, a Japan wax kernel oil, a montan wax, a coconut oil, a cured coconut oil, a tri-coconut oil fatty acid glyceride, a mutton tallow, a peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil. POE means polyoxyethylene. The same is applied to the following cases.

Illustrative example of the hydrocarbon oil includes a linear, a branched, and a volatile hydrocarbon oil. Illustrative example of the hydrocarbon oil includes an ozocerite, an α-olefin oligomer, a soft isoparaffin, an isododecane, an isohexadecane, a light liquid isoparaffin, a squalane, a synthetic squalane, a vegetable squalane, a squalene, a ceresin, a paraffin, a paraffin wax, a polyethylene wax, a polyethylene/polypropylene wax, a (ethylene/propylene/styrene) copolymer, a (butylene/propylene/styrene) copolymer, a liquid paraffin, a liquid isoparaffin, a pristane, a polyisobutylene, a hydrogenerated polyisobutene, a microcrystalline wax, and a vaseline. Illustrative example of the higher fatty acids includes a lauric acid, a myristic acid, a palmitic acid, a stearic acid, a behenic acid, an undecylenic acid, an oleic acid, a linoleic acid, a linolenic acid, an arachidonic acid, an eicosapentaenoic acid (EPA), a docosahexaenoic acid (DHA), an isostearic acid, and a 12-hydroxystearic acid.

Illustrative example of the higher alcohol includes a lauryl alcohol, a myristyl alcohol, a palmityl alcohol, a stearyl alcohol, a behenyl alcohol, a hexadecyl alcohol, an oleyl alcohol, an isostearyl alcohol, a hexyl dodecanol, an octyl dodecanol, a cetostearyl alcohol, a 2-decyl tetradecynol, a cholesterol, a phytosterol, a POE cholesterol ether, a monostearyl glycerin ether (batyl alcohol), and a monooleyl glyceryl ether (selachyl alcohol).

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptyldecyl palmitate, cholesteryl 12-hydroxystearate, a dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, isopropylester lauroyl sarcosinate, and diisostearyl malate. Illustrative example of the glyceride oil includes acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

The cosmetic of the present invention may use, depending on the purpose thereof, at least one compound having an alcoholic hydroxyl group in a molecular structure. Illustrative example of the compound having an alcohol hydroxyl group that can be added in the present invention includes a lower alcohol such as ethanol and isopropyl alcohol; a sugar alcohol such as sorbitol and maltose; a sterol such as cholesterol, sitosterol, phytosterol, and lanosterol; and a polyvalent alcohol such as butyleneglycol, propyleneglycol, dibutyleneglycol, and pentylene glycol.

Preferably, the cosmetic of the present invention includes water and is in the form of an emulsion such as a water-in-oil emulsion, an oil-in-water emulsion, and a multi-emulsion such as W/O/W or O/W/O. Illustrative example of the emulsion cosmetic preferably includes a make-up base, a liquid foundation, a sunscreen emulsion, and a sunscreen cream.

Preferably, the cosmetic of the present invention includes a powder and is in the form of a liquid, a paste, or a solid, with the powder dispersed therein.

Any powder may be used provided that the powder is used in a usual cosmetic, regardless of its form (e.g., spherical, needle-like, and plate-like), its particle diameter (e.g., fumed, microparticle, and pigment-class), and its particle structure (e.g., porous, and non-porous). Illustrative example of the powder includes an inorganic powder, an organic powder, a surfactant metal salt powder, a color pigment, a pearl pigment, a metal powder pigment, a tar pigment, a natural dye, and a coloring agent such as a dye.

Illustrative example of the inorganic powder includes titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, lepidolite, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxyl apatite, vermiculite, higilite, bentonite, montmorillonite, hectorite, zeolite, ceramics powder, dibasic calcium phosphate, alumina, aluminum hydroxide, boron nitride, silica, and silica silylate.

Illustrative example of the organic powder includes a polyamide powder, polyacrylic acid/acrylic acid ester powder, a polyester powder, a polyethylene powder, a polypropylene powder, a polystyrene powder, a polyurethane powder, a benzoguanamine powder, a polymethyl benzoguanamine powder, a tetrafluoroethylene powder, a polymethyl methacrylate powder, a cellulose powder, a silk powder, a nylon powder, a 12 nylon and a 6 nylon, cross-linked spherical dimethylpolysiloxane fine powder having crosslinked dimethylpolysiloxane, crosslinked spherical polymetylsilsesquioxane fine powder, fine powder obtained by coating crosslinked spherical organopolysiloxane rubber surface with polymetylsilsesquioxane particle, hydrophobic silica, a styrene-acrylic acid copolymer, a divinyl benzene-styrene copolymer, a vinyl resin, a urea resin, a phenolic resin, a fluorinated resin, a silicone resin, an acryl resin, a melamine resin, an epoxy resin, a polycarbonate resin, a fine crystalline fiber powder, a starch powder, a fatty acid starch derivative powder, and lauroyl lysine.

Illustrative example of the surfactant metal salt powder (metal soap) includes zinc undecylenate, aluminum isostearate, zinc stearate, aluminum stearate, calcium stearate, magnesium stearate, zinc myristate, magnesium myristate, zinc cetylphosphate, calcium cetylphosphate, sodium cetylphosphate zinc, zinc palmitate, aluminum palmitate, and zinc laurate.

Illustrative example of the color pigment includes an inorganic red pigment such as iron oxide, iron hydroxide, and iron titanate; an inorganic brown pigment such as γ-iron oxide; an inorganic yellow pigment such as a yellow iron oxide and an ocher; an inorganic black pigment such as a black iron oxide and a carbon black; an inorganic purple pigment such as a manganese violet and a cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a synthetic resin powder obtained by hybridization of these powders.

Illustrative example of the pearl pigment includes a mica coated with titanium oxide, bismuth oxychloride, bismuth oxychloride coated with titanium oxide, a talc coated with titanium oxide, a fish scale, and a color mica coated with titanium oxide. Illustrative example of the metal powder pigment includes an aluminum powder, a copper powder, and a stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Illustrative example of the natural dye includes carminic acid, laccaic acid, carthamin, brazilin, and crocin.

Among these powders, in the present invention, a crosslinked spherical dimethylpolysiloxane fine powder at least part of which has crosslinked dimethylpolysiloxane, a crosslinked spherical polymetylsilsesquioxane fine powder, a fine powder obtained by coating the crosslinked spherical polysiloxane rubber surface with a polymetylsilsesquioxane particle, a fine powder obtained by coating the crosslinked spherical diphenylpolysiloxane rubber surface with a polymetylsilsesquioxane particle, and hydrophobic silica are preferable, and a powder having a fluorine group and colorants are used. Commercially available products thereof is KMP-590, KSP-100, KSP-101, KSP-102, KSP-105, and KSP-300 (all products from Shin-Etsu Chemical Co., Ltd.).

In addition, usable are a powder obtained by hybridizing, or treating these powders, with a general oil agent, a silicone oil, a fluorine-containing compound, a surfactant, and the like. These powders may be surface-treated in advance, for example, a fluorine-containing compound-treatment, a silicone resin-treatment, pendant-treatment, silane coupling agent-treatment, titanium coupling agent-treatment, an oil agent-treatment, N-acyl lysine-treatment, polyacrylic acid-treatment, metallic soap-treatment, amino acid-treatment, inorganic compound-treatment, plasma-treatment, and mechanochemical-treatment, and as required, at least one thereof may be used. These powders are preferably used in an amount of 99% by mass or less, relative to the total amount of the cosmetic. In particular, these powders are preferably used in an amount of 70 to 99% by mass, relative to the total amount of the cosmetic in the case of powder cosmetic.

The cosmetic of the present invention may further include an organic UV-absorber. Illustrative example of the organic UV-absorber includes a benzoic acid UV-absorber such as para-amino benzoic acid; an anthranilic acid UV-absorber such as methyl anthranilate; a salicylic UV-absorber such as methyl salicylate; a cinnamic acid UV-absorber such as octyl para-methoxy cinnamate; a benzophenone UV-absorber such as 2,4-dihydroxybenzophenone; a urocanic acid UV-absorber such as ethyl urocanate; and a dibenzoylmethane UV-absorber such as 4-t-butyl-4'-methoxy-dibenzoylmethane.

The cosmetic of the present invention may also contain, depending on the purpose thereof, surfactants. Accordingly, the cosmetic is an emulsion-type having excellent usability. As to the surfactants like this, there are an anionic, a cationic, a nonionic and an amphoteric surfactant; and in the present invention, there is no particular restriction, and thus any of these may be used provided that the surfactant is used in a usual cosmetic.

Illustrative example of the anionic surfactant includes a fatty acid soap such as sodium stearate and triethanolamine palmitate, an alkyl ether carboxylic acid and a salt thereof, a condensate between an amino acid and a fatty acid, an alkane sulfonate, an alkene sulfonate, a sulfonate of a fatty acid ester, a sulfonate of a fatty acid amide, a sulfonate of a formalin condensate, an alkyl sulfate ester salt, a sulfate ester salt of a higher secondary alcohol, a sulfate ester salt of an alkyl and an allyl ether, a sulfate ester salt of a fatty acid ester, a sulfate ester salt of a fatty acid alkylolamide, a sulfate ester salt of a Turkey red oil and so on, an alkyl phosphate salt, an ether phosphate salt, an alkyl allyl ether phosphate salt, an amide phosphate salt, N-acyl lactate, N-acyl sarcosinate, and an N-acylamino acid activator. Illustrative example of the cationic surfactant includes an amine salt such as an alkylamine salt, a polyamine and an amino alcohol fatty acid derivative; an alkyl quaternary ammonium salt, an aromatic quaternary ammonium salt, a pyridinium salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a methyl glycoside fatty ester, alkyl polyglucoside, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytostanol ether, a polyoxyethylene phytosterol ether, a polyoxyethylene cholestanol ether, a polyoxyethylene cholesteryl ether, a linear or a branched polyoxyalkylene-modified organopolysiloxane, a linear or a branched organopolysiloxane co-modified with a polyoxyalkylene and an alkyl, a linear or a branched organopolysiloxane modified with a poly glycerin, a linear or a branched organopolysiloxane co-modified with a polyglycerin and an alkyl, an alkanol amide, a sugar ether, and a sugar amide.

Illustrative example of the amphoteric surfactant includes a betaine, an aminocarboxylic acid salt, an imidazoline derivative, and an amido amine.

Among these surfactants, a linear or a branched organopolysiloxane having a polyoxyethylene chain or a polyglycerin chain in its molecular structure, or an alkyl-comodified organopolysiloxane thereof is preferable. Commercially available products thereof are not particularly restricted, but KF-6011, KF-6011P, KF-6043, KF-6012, KF-6013, KF-6015, KF-6016, KF-6017, KF-6028, KF-6028P, KF-6038, KF-6048, KF-6100, KF-6104, and KF-6105 (all products from Shin-Etsu Chemical Co., Ltd.) are preferable. A surfactant having an HLB of 2 to 10 is preferable, and used in an amount of 0.1 to 20% by mass, relative to the total amount of the cosmetic, particularly in an amount of 0.2 to 10% by mass.

The cosmetic of the present invention may contain a composition composed of a crosslinked organopolysiloxane polymer having no hydrophilic group and a liquid oil agent. The crosslinked organopolysiloxane polymer is obtained by the reaction of an alkyl hydrogen polysiloxane and a crosslinking agent having a reactive vinyl unsaturated group at a chain end. Illustrative example of the alkyl hydrogen polysiloxane includes methyl hydrogen polysiloxane having a linear or a partial branch unit, and methyl hydrogen polysiloxane grafted with an alkyl chain having 6 to 20 carbon atoms. Two or more hydrogen atoms bonded to a silicon atom are required in a molecule on average. Illustrative example of the crosslinking agent includes those having two or more vinyl reaction sites in a molecule such as methyl vinylpolysiloxane and $\alpha, \omega$-alkenyl diene, as shown in compositions disclosed in Japanese Patent No. 1925781, Japanese Patent No. 1932769, WO03-24413, and Japanese Patent Laid-Open Publication (Kokai) No. 2009-185296. The crosslinked methylpolysiloxane is swollen with e.g., a low viscous silicone the amount of which is own weight or more of the crosslinking organopolysiloxane at 0.65 mm$^2$/s (25° C.) to 100.0 mm$^2$/s (25° C.), liquid paraffin, squalan, a hydrocarbon oil such as isododecane, and glyceride oil such as trioctanoin, and ester oil. Commercially available products of the crosslinked organopolysiloxane are not particularly restricted, but KSG-15, KSG-16, KSG-18, KSG-1610, and USG-103 in the form of a paste with a silicone oil, and USG-106, KSG-41, KSG-42, KSG-43, KSG-44, and KSG-810 in the form of a paste with a hydrocarbon oil or a triglyceride oil (all products from Shin-Etsu Chemical Co., Ltd.) are preferable. The composition composed of the crosslinked organopolysiloxane having no hydrophilic group and a liquid oil agent is used preferably in an amount of 0.1 to 50% by mass, relative to the total amount of the cosmetic, more preferably 1 to 30% by mass.

The cosmetic of the present invention may further include a composition composed of a hydrophilic crosslinking organopolysiloxane polymer and a liquid oil agent. Preferable illustrative example of the hydrophilic group includes a polyether group and a polyglyceryl group. The crosslinked organopolysiloxane polymer having a polyether group and/or a polyglyceryl group is obtained by the reaction of an alkyl hydrogen polysiloxane and a crosslinking agent having a reactive vinyl unsaturated group at a chain end. Illustrative example of the alkyl hydrogen polysiloxane includes a methyl hydrogen polysiloxane grafted with a polyoxyethylene chain and a methyl hydrogen polysiloxane grafted with a polyglyceryl chain. Two or more hydrogen atoms bonded to a silicon atom are required in a molecule on average. Illustrative example of the crosslinking agent includes those having two or more vinyl reaction sites in a molecule such as methylvinylpolysiloxane, $\alpha, \omega$-alkenyldiene, glycerine triallylether, polyoxyalkynyl glycerine triallylether, trimethylolpropanetriallyl ether, and polyoxyalkynyl trimethylolpropanetriallyl ether. Crosslinked products by the reaction of these substances may have at least one hydrophilic group, and the compositions are preferably disclosed in Japanese Patent No. 2631772, Japanese Patent Laid-Open Publication (Kokai) No. H09-136813, Japanese Patent Laid-Open Publication (Kokai) No. 2001-342255, WO03/20828, and Japanese Patent Laid-Open Publication (Kokai) No. 2009-185296. The crosslinked organopolysiloxane polymer is swollen to a low viscous silicone the amount of which is own weight or more of the crosslinked organopolysiloxane at 0.65 mm$^2$/s (25° C.) to 100.0 mm$^2$/s (25° C.), liquid paraffin, squalan, a hydrocarbon oil such as isododecane, a glyceride oil such as trioctanoin, or an ester oil. Commercially available products of the crosslinked organopolysiloxane are not particularly restricted, but KSG-210, KSG-240, and KSG-710 in the form of a paste with a silicone oil, and KSG-310, KSG-320, KSG-330, KSG-340, KSG-820, KSG-830, and KSG-840 in the form of a paste with a hydrocarbon oil or a triglyceride oil (all products from Shin-Etsu Chemical Co., Ltd.) are preferable. The composition composed of the hydrophilic crosslinking organopolysiloxane and a liquid oil agent is preferably used in an amount of 0.1 to 50% by mass, relative to the total amount of the cosmetic, more preferably in an amount of 1 to 30% by mass.

The cosmetic of the present invention may include a silicone resin. The silicone resin is preferably selected from the group consisting of a net-work silicone compound including an $SiO_2$ unit and/or an $RSiO_{1.5}$ (R represents a alkyl group), a linear acrylic/silicone graft copolymer, and a block copolymer of these compounds. The linear acrylic/silicone graft copolymer or the block copolymer may include at least one moiety selected from the group consisting of a pyrrolidone moiety, a long chain alkyl moiety, a polyoxyalkylene moiety, a fluoroalkyl moiety, and an anion moiety such as carboxylic acid. Commercially available products of the silicone resin are not particularly restricted, but KP-541, KP-543, KP-545, KP-549, KP-550, KP-571, KP-575, and KP-581 dissolved into a silicone oil, a hydrocarbon oil, or alcohol (all products from Shin-Etsu Chemical Co., Ltd.) are preferable.

The net-work silicone compound is preferably a net-work silicone compound denoted as MQ, MDQ, MT, MDT, or MDTQ. M, D, T, and Q denote an $R_3SiO_{0.5}$ unit, an $R_2SiO$ unit, an $RSiO_{1.5}$ unit, and an $SiO_2$ unit, respectively. The net-work silicone compound may include in a molecule at least one moiety selected from the group consisting of a pyrrolidone moiety, a long chain alkyl moiety, a polyoxyalkylene moiety, a fluoroalkyl moiety, and an amino moiety. Commercially available products of the net-work silicone compound are not particularly restricted, but KF-7312J, KF-7312K, and KF-7312T (all products from Shin-Etsu Chemical Co., Ltd.) are preferable.

The silicone resin may be dissolved into a low viscous silicone oil, a volatile silicone oil, or other solvents. In each of these oils, the silicone resin is preferably used in an amount of 0.1 to 20% by mass, relative to the total amount of the cosmetic of the present invention, more preferably in an amount of 1 to 10% by mass.

The cosmetic of the present invention is not particularly restricted, but preferable are a skin care cosmetic such as milky lotion, cream, cleansing, facial mask, massage cream, essence, emollient oil, cleansing agent, deodorizer, hand cream, lip cream, and antiwrinkle cream; a make-up cosmetic such as make-up base, concealer, face powder, and liquid foundation; a hair cosmetic such as shampoo, conditioner, treatment, and hair styling agent; and a UV care cosmetic such as antiperspirant, sunscreen oil, sunscreen emulsion, and sunscreen cream.

EXAMPLES

Synthesis Examples, Comparative Synthesis Examples, Examples and Comparative Examples of the cosmetic of the present invention will be described in detail, but the present invention is not restricted to the following Examples. Herein, unless otherwise noted, "%" means "% by mass" of each component relative to the total mass as 100%, and the degree of viscosity is measured at 25° C.

Synthesis Examples (1) to (3)

N-methylpyrrolidone (140.0 g), each of the radical reactive vinyl monomers shown in Table 1 and a t-butylperoxy-2-ethylhexanoate (4.0 g) were charged into a glass flask having a stirrer, a thermometer, and a reflex condenser, and stirred in stream of nitrogen and heated to reflux. The product was subjected to radical polymerization for 5 hours to obtain a vinylradical polymer reaction solution having a hydroxyl group. To the solution were added an N-methylpyrrolidone (90 g) and a triethylamine (4.0 g), and a tris (trimethyl siloxy)silylpropyl isocyanate was dropped therein at 120° C. to cause urethanization reaction for 10 hours. The reaction solution was subjected to reprecipitation treatment with water/methanol (1:9) to remove the unreacted monomer and a solvent, and dried under reduced pressure at 80° C. to obtain a urethane group-containing silicone vinyl polymer. Table 1 shows the results. The residual hydroxyl group was calculated and the molecular weight in terms of polystyrene was calculated by gel-permeation chromatography (GPC) with THF.

TABLE 1

| | Synthesis Example (1) | Synthesis Example (2) | Synthesis Example (3) |
|---|---|---|---|
| 2-hydroxyethyl methacrylate (g) | 70 | | 50 |
| 2-hydroxyethyl acrylamide (g) | | 90 | |
| Methyl methacrylate (g) | 30 | | 15 |
| n-stearyl methacrylate (g) | | 10 | |
| 2-ethylhexyl acrylate (g) | | | 35 |
| Tris(trimethylsiloxy) silylpropyl isocyanate (g) | 210 | 310 | 160 |
| Reaction rate of hydroxyl group (%) | 85 | 70 | 85 |
| Dried yield (g) | 240 | 285 | 210 |
| Number average molecular weight by GPC (in terms of polystyrene, Tosoh Corporation) | 55000 | 40000 | 30000 |

Comparative Synthesis Examples (1) to (4)

A 2-propanol (140.0 g), each of the radical reactive monomers and each of the silicone macromers shown in Table 2, and a t-butylperoxy-2-ethylhexanoate (4.0 g) were charged into a glass flask having a stirrer, a thermometer, and a reflex condenser, and stirred in stream of nitrogen and heated to reflux. The product was subjected to polymerization for 5 hours to obtain a silicone-containing vinyl polymer reaction solution. Then, the reaction solution was heated under reduced pressure at 140° C. to distill out a solvent and the unreacted monomer. Table 2 shows the resulting yield after stripping (distilled yield) and the molecular weight measured by GPC with THF.

TABLE 2

| | Comparative Synthesis Example (1) | Comparative Synthesis Example (2) | Comparative Synthesis Example (3) | Comparative Synthesis Example (4) |
|---|---|---|---|---|
| 2-hydroxyethyl methacrylate (g) | 10 | 10 | 10 | |
| 2-hydroxyethyl acrylamide (g) | | | | |
| Methyl methacrylate (g) | 30 | 30 | 30 | |
| n-stearyl methacrylate (g) | | | | 10 |
| 2-ethylhexyl acrylate (g) | | | | |
| Silicone macromer (1) (g) | 60 | | | |
| Silicone macromer (2) (g) | | 60 | | 90 |
| Silicone macromer (3) (g) | | | 60 | |
| Distilled yield (g) | 98 | 98 | 97 | 99 |
| Number average molecular weight by GPC (in terms of polystyrene, Tosoh Corporation) | 30000 | 35000 | 34000 | 22000 |

Silicone macromer (1)

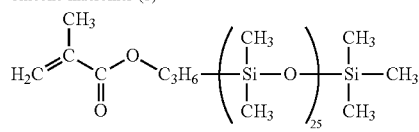

Silicone macromer (2)

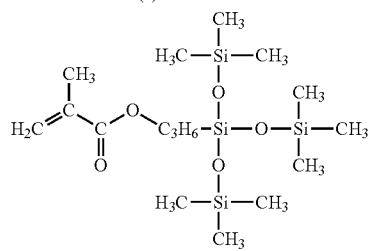

Silicone macromer (3)

TABLE 2-continued

|  | Comparative Synthesis Example (1) | Comparative Synthesis Example (2) | Comparative Synthesis Example (3) | Comparative Synthesis Example (4) |
|---|---|---|---|---|
|  |  |  |  | $CH_2{=}C(CH_3){-}C({=}O){-}O{-}C_3H_6{-}Si{-}\{O{-}Si(CH_3)_2{-}C_2H_4{-}Si{-}(O{-}Si(CH_3)_2{-}CH_3)_3\}_3$ |

Examples 1 to 4 and Comparative Examples 1 to 4

The following water-in-oil liquid foundations were prepared by a conventional method. The liquid foundations obtained were evaluated by the following method. Table 3 shows the results.

Evaluation Method

The emulsion stability of the liquid foundations at 50° C. three months after preparation was visually evaluated. The criteria are shown as follows.

- ⊚: Not separated
- ○: Slightly separated in upper layer
- Δ: Separated in upper layer
- ×: Separated in upper and lower layers After each liquid foundation was prepared, the cosmetic (2 g) was applied to the panel skin and sufficiently penetrated for evaluation. A sensory evaluation was carried out to find uniform hue, non-stickiness, favorable cosmetic durability (suppressed color transfer), light feeling on use, and easy cleansing removal. The results were evaluated according to the number of the panels who found the cosmetic "effective" on the questionnaire.

Criteria by Panel Number

- ⊚: 4 or 5 panels found the cosmetic "effective".
- ○: 3 panels found the cosmetic "effective".
- Δ: 2 panels found the cosmetic "effective".
- ×: 0 or 1 panel founds the cosmetic "effective".

TABLE 3

|  |  | Example | | | | Comparative Example | | | |
|---|---|---|---|---|---|---|---|---|---|
|  |  | 1 | 2 | 3 | 4 | 1 | 2 | 3 | 4 |
| 1 | Vinyl polymer of Synthesis Example 1 | 5 |  |  | 3 |  |  |  |  |
| 2 | Vinyl polymer of Synthesis Example 2 |  | 5 |  |  |  |  |  |  |
| 3 | Vinyl polymer of Synthesis Example 3 |  |  | 8 |  |  |  |  |  |
| 4 | Vinyl polymer of comparative Synthesis Example 1 |  |  |  |  | 5 |  |  |  |
| 5 | Vinyl polymer of comparative Synthesis Example 2 |  |  |  |  |  | 5 |  |  |
| 6 | Vinyl polymer of comparative Synthesis Example 3 |  |  |  |  |  |  | 3 |  |
| 7 | Vinyl polymer of comparative Synthesis Example 4 |  |  |  |  |  |  |  | 5 |
| 8 | KF-6017 *1 | 1 | 1 | 1 | 1 | 1 | 1 | 1 | 1 |
| 9 | Decamethyl cyclopentasiloxane | 30 | 30 | 30 | 30 | 30 | 30 | 30 | 30 |
| 10 | Dimethyl polysiloxane | 5 | 2 | 10 | 2 | 5 | 5 | 2 | 2 |
| 11 | Para-methoxy cinnamate 2-ethylhexyl |  | 3 |  | 3 |  |  | 3 | 3 |
| 12 | Montmorillonite modified with octadecyldimethylbenzyl ammonium salt | 4 | 4 | 4 | 4 | 4 | 4 | 4 | 4 |
| 13 | Hydrophobic titanium oxide *2 | 6 | 6 | 6 | 6 | 6 | 6 | 6 | 6 |
| 14 | Hydrophobic talc *2 | 3 | 3 | 3 | 3 | 3 | 3 | 3 | 3 |
| 15 | Hydrophobic mica *2 | 2 | 2 | 2 | 2 | 2 | 2 | 2 | 2 |
| 16 | Hydrophobic colcothar *2 | 1.5 | 1.5 | 1.5 | 1.5 | 1.5 | 1.5 | 1.5 | 1.5 |
| 17 | Hydrophobic black iron oxide *2 | 0.7 | 0.7 | 0.7 | 0.7 | 0.7 | 0.7 | 0.7 | 0.7 |
| 18 | Hydrophobic yellow iron oxide *2 | 0.2 | 0.2 | 0.2 | 0.2 | 0.2 | 0.2 | 0.2 | 0.2 |
| 19 | dipropylene glycol | 5 | 5 | 5 | 5 | 5 | 5 | 5 | 5 |
| 20 | Fragrance | Moderate | Moderate | Moderate | Moderate | Moderate | Moderate | Moderate | Moderate |

TABLE 3-continued

|  |  | Example | | | | Comparative Example | | | |
| --- | --- | --- | --- | --- | --- | --- | --- | --- | --- |
|  |  | 1 | 2 | 3 | 4 | 1 | 2 | 3 | 4 |
| 21 |  Purified water | Residual | Residual | Residual | Residual | Residual | Residual | Residual | Residual |
| Evaluation | Emulsion stability at 50° C. three months after preparation | ⊚ | ⊚ | ⊚ | ○ | Δ | ○ | Δ | Δ |
|  | Uniform hue | ⊚ | ○ | ○ | ⊚ | ○ | Δ | Δ | Δ |
|  | Non-stickiness | ⊚ | ○ | ⊚ | ○ | Δ | X | ○ | X |
|  | Cosmetic Durability | ⊚ | ⊚ | ⊚ | ○ | Δ | Δ | ○ | X |
|  | Light feeling on use | ⊚ | ○ | ○ | ⊚ | Δ | Δ | Δ | Δ |
|  | Easy cleansing removal | ⊚ | ⊚ | ○ | ⊚ | X | Δ | X | ○ |

*1: KF-6017, polyether-modified silicone, Product from Shin-Etsu Chemical Co., Ltd.
*2: Hydrophobic treatment, adding 2% methyl hydrogen polysiloxane to a powder and heating As shown above, the liquid foundations of Examples 1 to 4 show higher emulsion stability than those of Comparative Examples 1 to 4, and are more excellent in uniform hue, non-stickiness, cosmetic durability (suppressed color transfer), light feeling on use, and easy cleansing removal.

Examples 5 and 6 and Comparative Examples 5 and 6

The following powder foundations were prepared by a conventional method. The powder foundations obtained were evaluated by the following method. Table 4 shows the results.

After each powder foundation was prepared, the cosmetic was applied to the panel skin and sufficiently penetrated for evaluation. A sensory evaluation was carried out to find uniform smooth spreadability, non-stickiness, and cosmetic durability (suppressed color transfer). The results were evaluated according to the number of the panels who found the cosmetic "effective" on the questionnaire.
Criteria by Panel Number
⊚: 4 or 5 panels found the cosmetic "effective".
○: 3 panels found the cosmetic "effective".
Δ: 2 panels found the cosmetic "effective".
×: 0 or 1 panel found the cosmetic "effective".

TABLE 4

|  |  | Example | | Comparative Example | |
| --- | --- | --- | --- | --- | --- |
|  |  | 5 | 6 | 5 | 6 |
| 1 | Vinyl polymer of Synthesis Example 1 | 1.5 |  |  |  |
| 2 | Vinyl polymer of Synthesis Example 2 |  | 2 |  |  |
| 3 | Vinyl polymer of Comparative Synthesis Example 1 |  |  | 1.5 |  |
| 4 | Vinyl polymer of Comparative Synthesis Example 4 |  |  |  | 2 |
| 5 | Titanium oxide treated with silicone *1 | 12 | 12 | 12 | 12 |
| 6 | Sericite treated with silicone *1 | 35 | 35 | 35 | 35 |
| 7 | Talc treated with lecithin | 35.1 | 35.1 | 35.1 | 35.1 |
| 8 | Spherical nylon powder treated with lecithin | 5 | 5 | 5 | 5 |
| 9 | Colcothar treated with silicone | 0.4 | 0.4 | 0.4 | 0.4 |
| 10 | Yellow iron oxide treated with silicone *1 | 2 | 2 | 2 | 2 |
| 11 | Ambergris treated with silicone *1 | 0.4 | 0.4 | 0.4 | 0.4 |
| 12 | Black iron oxide treated with silicone *1 | 0.1 | 0.1 | 0.1 | 0.1 |
| 13 | Crosslinked dimethyl polysiloxane *2 | 4 | 3 | 4 | 3 |
| 14 | Glyceryl trioctanoate | 1.5 | 1.5 | 1.5 | 1.5 |
| 15 | Silicone wax *3 | 1.5 | 1.5 | 1.5 | 1.5 |
| 16 | Dimethyl polysiloxane (6 mm$^2$/s) | 1.5 | 2 | 1.5 | 2 |
| Evaluation | Smooth spreadability | ⊚ | ⊚ | Δ | ○ |
|  | Cosmetic durabilitiy | ⊚ | ⊚ | Δ | Δ |
|  | Non-stickiness | ⊚ | ○ | ○ | Δ |

*1: KF-9909-treated product: Product from Shin-Etsu Chemical Co., Ltd.
*2: KSG-16: Product from Shin-Etsu Chemical Co., Ltd.
*3: KP-561P: Product from Shin-Etsu Chemical Co., Ltd.

As shown above, the powder foundations of Examples 5 and 6 show more favorable spreadability than those of Comparative Examples 5 and 6, and are more excellent in non-stickiness, suppressed color transfer, and excellent in cosmetic durability.

(Example 7) Cream Lipstick

| No. | Component | Mass (%) |
| --- | --- | --- |
| 1 | Dextrin palmitate/ethylhexanoate (Note 1) | 9.0 |
| 2 | Triethyl hexanoin | 7.0 |
| 3 | Vinyl polymer of Synthesis Example 3 | 8.0 |
| 4 | Alkyl-modified crosslinked dimethyl polysiloxane (Note 2) | 8.0 |
| 5 | Alkyl-modified branched polyglycerin-modified polysiloxane (Note 3) | 2.0 |
| 6 | Decamethyl cyclopentasiloxane | 35.0 |
| 7 | 1,3-butylene glycol | 4.8 |
| 8 | Purified water | 18.0 |

-continued

| No. | Component | Mass (%) |
| --- | --- | --- |
| 9 | Color pigment | 6.0 |
| 10 | Mica | 2.0 |
| 11 | Fragrance | 0.2 |
| | Total | 100.0 |

(Note 1):
Rheopearl TT, Product from Chiba Flour Milling
(Note 2):
KSG-43, Product from Shin-Etsu Chemical Co., Ltd.
(Note 3):
KF-6105, Product from Shin-Etsu Chemical Co., Ltd.

Preparation of Cosmetic
A: Part of the components 1 and 2 and the components 3 to 6 were heated to be uniformly mixed.
B: The component 9 was mixed with the residue of the component 2, dispersed with a roller, and added to the component A to be uniformly mixed.
C: The components 7 and 8 were mixed, heated and added to the component B to be emulsified.
D: The components 10 and 11 were added to the component C to obtain a cream lipstick.

The cream lipstick thus obtained provided smooth spreadability, non-stickiness, suppressed color transfer, and favorable cosmetic durability.

(Example 8) Hair Treatment

| No. | Composition | Mass (%) |
| --- | --- | --- |
| 1 | Silicone gum dissolved product (Note 1) | 5.0 |
| 2 | Diphenyl dimethicone (Note 2) | 4.0 |
| 3 | Vinyl polymer of Synthesis Example 2 | 1.0 |
| 4 | Cetyl octanoate | 1.0 |
| 5 | Polyether-modified silicone (Note 3) | 1.0 |
| 6 | PEG-60 hydrogenated cured castor oil | 1.0 |
| 7 | Glyceryl monostearate | 0.5 |
| 8 | Carboxy vinyl polymer (1% by mass solution) | 25.0 |
| 9 | Xanthan gum (1% by mass solution) | 7.0 |
| 10 | 1,3-butylene glycol | 5.0 |
| 11 | Alcohol | 7.0 |
| 12 | Preservative | 0.5 |
| 13 | Fragrance | 0.2 |
| 14 | Purified water | Residual |
| | Total | 100.0 |

(Note 1):
MK-15H; Product from Shin-Etsu Chemical Co., Ltd.
(Note 2):
KF-54; Product from Shin-Etsu Chemical Co., Ltd.
(Note 3):
KF-6013; Product from Shin-Etsu Chemical Co., Ltd.

Preparation of Cosmetic
A: The components 1 to 7 were heated and dissolved.
B: The components 10 to 14 were heated and dissolved.
C: The component B was added to the component A while stirring to be emulsified, and the components 8 and 9 were added thereto to obtain a hair treatment.

The hair treatment thus obtained provided smooth spreadability, and made the hair glossy and smooth.

While this invention has been described with an emphasis upon preferred embodiments, it will be obvious to those of ordinary skill in the art that variations of the preferred embodiments may be used and that it is intended that the invention may be practiced otherwise than as specifically described herein.

Accordingly, this invention includes all modifications encompassed within the spirit and scope of the invention as defined by the following claims.

What is claimed is:
1. A cosmetic comprising:
a urethane group-containing silicone vinyl polymer that is a urethanization reaction product of (a) a radical polymer having a hydroxyl group, the radical polymer being derived from a radical reactive vinyl monomer, and (b) an isocyanate silicone represented by the following general formula (1),

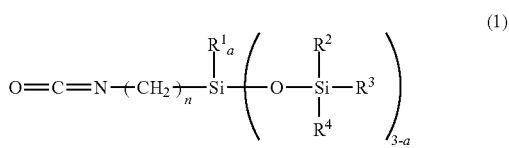

where each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3; and
water,
wherein:
the radical polymer is derived from: (i) at least one radical reactive vinyl monomer having a hydroxyl group that is an alkyl (meth)acrylate having a hydroxyl group and/or hydroxyethyl acrylamide, and/or glyceryl (meth)acrylate, and (ii) a higher alkyl (meth)acrylate having 8 or more carbon atoms,
a content of a unit derived from the isocyanate silicone represented by the general formula (1) in the urethane group-containing silicone vinyl polymer is 40 wt % or more,
the urethane group-containing silicone vinyl polymer includes at least one hydroxyl group, and
the cosmetic is in the form of an emulsion.
2. The cosmetic according to claim 1, wherein the (a) radical polymer is derived from at least one radical reactive vinyl monomer having a hydroxyl group selected from any of hydroxyethyl (meth)acrylate, hydroxypropyl (meth)acrylate, glyceryl (meth)acrylate, and hydroxyethyl acrylamide.
3. The cosmetic according to claim 1, wherein a content of the urethane group-containing silicone vinyl polymer is 0.05 to 40 wt %, relative to a total amount of the cosmetic.
4. The cosmetic according to claim 2, wherein a content of the urethane group-containing silicone vinyl polymer is 0.05 to 40 wt %, relative to a total amount of the cosmetic.
5. The cosmetic according to claim 1, further comprising a silicone oil.
6. The cosmetic according to claim 2, further comprising a silicone oil.
7. The cosmetic according to claim 1, further comprising a powder.
8. The cosmetic according to claim 2, further comprising a powder.
9. A method for manufacturing a cosmetic of claim 1 comprising, in the order mentioned, the steps of:
(A) obtaining a radical polymer having a hydroxyl group by radical polymerization of (i) at least one radical reactive vinyl monomer having a hydroxyl group that is an alkyl (meth)acrylate having a hydroxyl group and/or hydroxyethyl acrylamide and/or glyceryl (meth)acrylate, and (ii) a higher alkyl (meth)acrylate having 8 or more carbon atoms, (B) obtaining a urethane group-containing silicone vinyl polymer by urethanization reaction of the radical polymer having a hydroxyl group and an isocyanate silicone represented by the following general formula (1) in the presence of a urethanization catalyst,

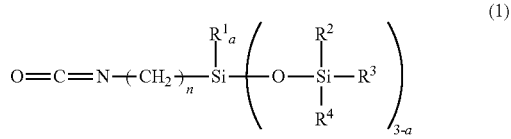

wherein, each of $R^1$, $R^2$, $R^3$, and $R^4$ independently represents any of an alkyl group having 1 to 8 carbon atoms, a fluorine-substituted alkyl group having 1 to 8 carbon atoms, and an aryl group having 6 to 12 carbon atoms; "n" represents a number of 1 to 10; and "a" represents a number of 0 to 3; and (C) forming a cosmetic by combining the urethane group-containing silicone vinyl polymer and water, wherein:

the cosmetic is in the form of an emulsion, a content of a unit derived from the isocyanate silicone represented by the general formula (1) in the urethane group-containing silicone vinyl polymer is 40 wt % or more, and the urethane group-containing silicone vinyl polymer includes at least one hydroxyl group.

10. The method for manufacturing a cosmetic according to claim 9, wherein in the step (A), at least one monomer selected from any of hydroxyethyl (meth) acrylate, hydroxypropyl (meth) acrylate, glyceryl (meth) acrylate, and hydroxyethyl acrylamide is used as the radical reactive vinyl monomer.

11. The method for manufacturing a cosmetic according to claim 9, wherein the urethanization catalyst is a tertiary amine.

12. The method for manufacturing a cosmetic according to claim 10, wherein the urethanization catalyst is a tertiary amine.

* * * * *